United States Patent [19]

Agerup et al.

[11] Patent Number: 5,128,341
[45] Date of Patent: Jul. 7, 1992

[54] USE OF β-RECEPTOR BLOCKING AGENTS

[75] Inventors: Bengt Ågerup, Uppsala; Fredrik Aust, Västra Frölunda, both of Sweden

[73] Assignee: Bengt Ågerup, Uppsala, Sweden

[21] Appl. No.: 671,794

[22] PCT Filed: Jul. 25, 1990

[86] PCT No.: PCT/SE90/00504
§ 371 Date: Mar. 29, 1991
§ 102(e) Date: Mar. 29, 1991

[87] PCT Pub. No.: WO91/01725
PCT Pub. Date: Feb. 21, 1991

[30] Foreign Application Priority Data

Jul. 31, 1989 [SE] Sweden .................. 8902629

[51] Int. Cl.⁵ ............... A61K 31/535; A61K 31/405; A61K 31/18; A61K 31/135
[52] U.S. Cl. ............... 514/236.2; 514/415; 514/605; 514/652; 514/231.5
[58] Field of Search ............ 514/231.5, 415, 605, 514/652, 236.2

[56] References Cited

U.S. PATENT DOCUMENTS 4,428,883  1/1984  Hussain .................. 424/248.51

FOREIGN PATENT DOCUMENTS 945095  12/1963  United Kingdom .

OTHER PUBLICATIONS

Otolaryngology-Head and Neck Surgery, vol. 96, 1987, L. Harker et al: "Episodic vertigo in basilar artery migraine", pp. 239-250, (entire article).
Chemical Abstracts, vol. 110, No. 1, 2 Feb. 1989, (Columbus, Ohio, US), N Kobayashi et al: "Effects of beta-agonists and beta antagonist on the cochlear blood flow", see, abstract 562z, & Ear Res. Jpn. 1988, 19, 480-2.
JAMA, vol. 252, No. 18, Nov. 1984 D. J. Dalsessio: "Beta-blockers and migraine", p. 2614—entire article.

*Primary Examiner*—Frederick E. Waddell
*Assistant Examiner*—Kimberly R. Jordan
*Attorney, Agent, or Firm*—Browdy and Neimark

[57] ABSTRACT

The present invention relates to a novel use of β-receptor blocking agents for preparation of a drug for treatment of Ménière's disease.

4 Claims, 1 Drawing Sheet

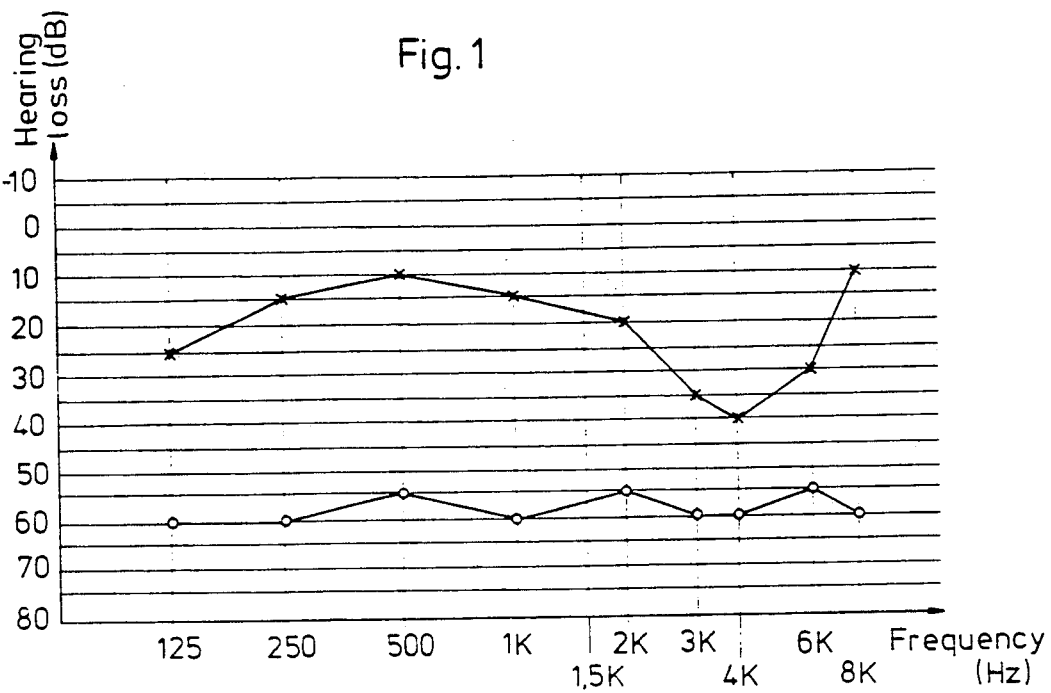
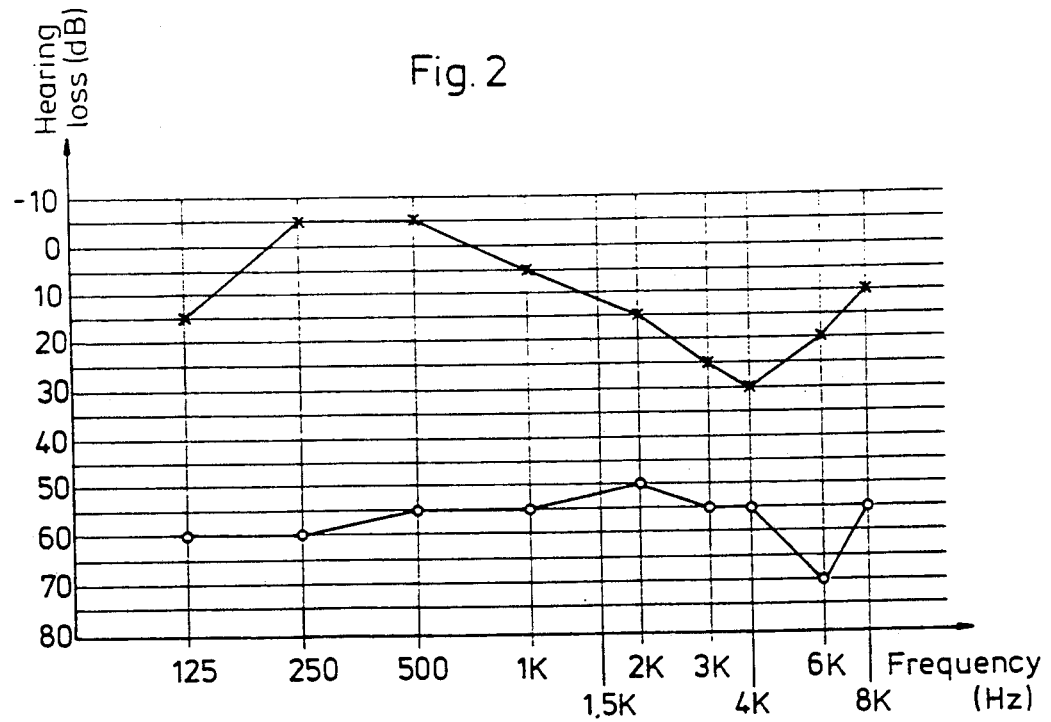

USE OF β-RECEPTOR BLOCKING AGENTS

The present invention relates to a novel use of β-receptor blocking agents, more specifically, the present invention relates to a method of treating Meniere's disease and use of β-receptor blocking agents for preparation of a drug for treatment of Menieres disease.

BACKGROUND OF THE INVENTION

Meniere's disease affects the organs of hearing and balance positioned in the labyrinth of the inner ear. The symptoms are periodic attacks of severe vertigo and balance disorders, tinnitus, a saturated or pressurized sensation of the ear, intolerance versus noice and diplacusis, and also severe perspiration, headache and nausea, the latter symptoms reminding one of side effects when overdosing β-receptor blocking agents. In almost every case, the disease results in permanent hearing loss.

The etiology of the disease is unknown. A theory is that it is associated with a disorder of the osmotic pressure gradient at the blood endolymph barrier. Finally, endolymphatic pressure or chemical imbalance causes permanent hairy-cell damage and deafness. Another theory is that labyrinth cracking alleviates or provokes the vertigo attacks mixing the perilymph and endolymph. During the attack free periods, the patients do not show any disorders accept for the hearing loss. The cause of the hearing loss is believed to be due to an increased pressure in the endolymph and this explains the latin name of the disease, hydrops labyrinthi. As the endolymph volume increases the labyrinth swells resulting in hearing loss and vertigo.

There exists no conventional cure for Meniere's disease. However, patients having a milder form of the disease receive tranquilizers against vertigo provoked anxiety reactions. Further, antihistamines, diuretics and vascular dilatating drugs are administered which do not, per se, affect the inner ear but improve the patient's well-being. In more severe cases, the only solution hitherto has been surgery to destroy the diseased labyrinth in a one time operation or removing endolymph in repeated operations. When performing this destructive surgery, it is necessary that the other labyrinth be healthy to avoid patient deafness. Also, surgical procedures are known not affecting the hearing but these are not always successful. In the case of bilateral Meniere's disease both the vestibular labyrinths can be destroyed by parenteral administration of streptomycin requiring hospitalization of the patient during one or more weeks. Without surgery or other treatment, the labyrinth is destroyed with increasing age.

β-receptor blocking agents have hitherto not been given to patients with audiologic diseases, such as Meniere's disease. In fact, they have never even been considered as a possible cure for Meniere's disease. As an example of this, we refer to "Otolaryngol Head and Neck Surgery", Vol 96, 1987, pages 239-249, in which β-receptor blocking agents are suggested for prophylactic treatment of migraine but, in the case with patients having Meniere-like symptoms, only after the diagnosis of Meniere's disease has been ruled out by audiography.

The most common indications for β-receptor blocking agents today are: cardio-vascular diseases, e.g. hypertension and angina pectoris neurological diseases, e.g. migraine and tremor.

SUMMARY OF THE INVENTION

It is an object of the present invention to provide a treatment of Meniere's disease which improves both the above mentioned attacks and the hearing losses.

Another object is to relieve the Meniere patients, including the more severe cases, of their symptoms without surgery.

According to the present invention, these objects are achieved by the characterizing features of claim 1.

BRIEF DESCRIPTION OF THE DRAWINGS

The invention will be described more closely below with reference to the accompanying drawings, in which FIG. 1 is an audiogramme showing two curves representing the left and right ear, respectively, of a typical Meniere patient; and FIG. 2 is an audiogramme performed on the same patient as above subsequent to treatment according to the present invention.

According to the invention, Meniere patients are treated with β-receptor blocking agents. The patients receive a dosage commonly given to hypertensive patients. Preferably, non-selective $\beta_1 + \beta_2$ receptor blocking agents are used. The performance of selective $\beta_1$ receptor blocking agents is not as good as that of the non-selectives. Examples of $\beta_1 + \beta_2$ receptor blocking substances are: alprenolol, nadolol, oxprenolol, pindolol, propranolol, sotalol and timolol. A preferred β-receptor blocking substance is timolol, preferably administered at a dosage range of from about 10 mg to about 30 mg a day. This range is, of course, not to be construed as limiting.

FIG. 1 shows an audiogramme of a typical Meniere patient, the lower curve representing the right ear and the upper curve the left ear. The frequency in Hz is given on the x-axis and the hearing loss in dB is given on the y-axis. It appears that the patient is practically deaf on the right ear but this can have other causes than the disease, such as old age. The hearing ability of the patient is primarily decreased in the lower frequency region in which, inter alia, human speech is located. In addition to hearing loss, the patient also suffers from the typical Meniere symptoms, such as severe vertigo, tinnitus, nausea and headache.

FIG. 2 shows an audiogramme taken about 20 days after the FIG. 1 audiogramme of the same patient. In this time he has been treated with β-blocking agents according to the invention. The right ear has not appreciably changed its hearing ability while, on the other hand, the left ear has clearly improved, especially in the lower frequency range. Now, the patient has a hearing improvement of 10 dB at 125 Hz, of 20 dB at 250 Hz, of 15 dB att 500 Hz and of 10 dB at 1000 Hz. A hearing improvement is considered present if the hearing loss has decreased at least three frequencies.

DETAILED DESCRIPTION OF THE INVENTION

The effects of the treatment according to the invention are especially clearly demonstrated with reference to Table 1 below. The first column shows audiographic data of the initial hearing loss of a patient diagnosed with Meniere's disease. In addition to the severe hearing loss on his right ear he also suffered from tinnitus, vertigo and a pressurized sensation of the ear. The second column lists audiography data obtained 1 week after the first audiography. During this time the patient received blocking agents according to the invention. In addition to the improved hearing on the right ear the patient no longer suffered from vertigo or tinnitus. Then, the patient requested to stop the medication and after 1 month from the final doses of β-blocking agents the data listed in the third column were obtained. From the dB-values in this column, it appears that the hearing ability of the right ear is as bad as it was initially before commencing the treatment. Simultaneously, the patient regained his initial symptoms, such as vertigo, tinnitus and the pressurized sensation of the ear. Therefore, the patient again received β-blocking agents. A month later, the patient was fully recovered both with respect to his hearing ability and his other symptoms. When comparing the second and fourth columns, it appears that the hearing improvement is slightly better after one month treatment than after one week.

TABLE 1

| Frequency | Hearing loss (in dB) | | | | | | | |
|---|---|---|---|---|---|---|---|---|
| | Initial | | 1 week with t* | | 1 month without t* | | 1 month with renewed t* | |
| | L | R | L | R | L | R | L | R |
| 125 Hz | 5 | 45 | 10 | 25 | 10 | 45 | 5 | 10 |
| 250 Hz | 5 | 45 | 10 | 30 | 2 | 35 | 0 | 5 |
| 500 Hz | 0 | 45 | 0 | 10 | 0 | 45 | 0 | 5 |
| 1000 Hz | 5 | 35 | 0 | 0 | 0 | 40 | 0 | 0 |
| 2000 Hz | 0 | 25 | 0 | 15 | 5 | 30 | 0 | 15 |
| 3000 Hz | 0 | 10 | 0 | 0 | 0 | 10 | ND | ND |
| 4000 Hz | 0 | 0 | 0 | 0 | 0 | 15 | 10 | 5 |

L = left ear, R = right ear, ND = not determined
t* = treatment according to the invention Follow-up of the ongoing treatment according to the invention, performed several months after the onset of the treatment, showed that the earlier showed effects persisted in all the studied cases and that the condition of the patients were stable.

The surprising effect of β-receptor blocking agents on Meniere's disease is presumably due to a lowering of the pressure in the inner ear. It cannot be excluded that there exists a β-receptor in the inner ear which is not cardio-selective. Paradoxically, also the other symptoms of the Meniere patients are eliminated which, as already mentioned, remind one of the commonly present side effects of β-receptor blocking agents.

Thus, the present invention is directed to a totally new use of β-receptor blocking agents, namely for treatment of Meniere's disease.

We claim:

1. A method for treating a patient suffering from Ménierè's disease comprising administering to said patient an effective amount of a β-receptor blocking compound to relieve the symptoms of Ménierè's disease.

2. The method according to claim 1 wherein the β-receptor blocking agent is a β1+β2 receptor blocking agent.

3. The method according to claim 2 wherein the β-receptor blocking agent is selected from the group consisting of alprenolol, nadolol, exprenolol, pindolol, propranolol, sotalol and timolol.

4. The method according to claim 3 wherein the β-receptor blocking agent is timolol administered in a dosage of 10-30 mg per day.

* * * * *